US009788926B2

(12) United States Patent
Franke et al.

(10) Patent No.: US 9,788,926 B2
(45) Date of Patent: Oct. 17, 2017

(54) PERSONAL HYGIENE IMPLEMENT

(71) Applicant: Braun GmbH, Kronberg (DE)

(72) Inventors: Sven Alexander Franke, Darmstadt (DE); Alexander Franz Doll, Kronberg (DE); Robert Florian Schütz, Wiesbaden (DE)

(73) Assignee: BRAUN GMBH, Kronberg (DE)

( * ) Notice: Subject to any disclaimer, the term of this patent is extended or adjusted under 35 U.S.C. 154(b) by 377 days.

(21) Appl. No.: 14/573,471

(22) Filed: Dec. 17, 2014

(65) Prior Publication Data

US 2015/0173873 A1 Jun. 25, 2015

Related U.S. Application Data

(60) Provisional application No. 61/920,476, filed on Dec. 24, 2013.

(51) Int. Cl.

| | |
|---|---|
| *A61C 17/22* | (2006.01) |
| *A46B 13/04* | (2006.01) |
| *A46B 11/00* | (2006.01) |
| *A61C 17/34* | (2006.01) |
| *A61C 17/36* | (2006.01) |
| *A61C 17/028* | (2006.01) |

(52) U.S. Cl.
CPC ........ *A61C 17/227* (2013.01); *A46B 11/0006* (2013.01); *A46B 11/0055* (2013.01); *A46B 13/04* (2013.01); *A61C 17/3436* (2013.01); *A61C 17/36* (2013.01); *A61C 17/028* (2013.01)

(58) Field of Classification Search
CPC ... A61C 17/227; A61C 17/3436; A61C 17/36; A46B 11/0006; A46B 11/0055; A46B 13/04

See application file for complete search history.

(56) References Cited

U.S. PATENT DOCUMENTS

| | | | |
|---|---|---|---|
| 4,317,530 | A | 3/1982 | Magrath |
| 5,396,678 | A | 3/1995 | Bredall et al. |
| 5,836,769 | A | 11/1998 | Spencer |
| 6,041,467 | A | 3/2000 | Roberts et al. |
| 6,058,541 | A | 5/2000 | Masterman et al. |
| 6,108,851 | A | 8/2000 | Bredall et al. |
| 6,151,745 | A | 11/2000 | Roberts et al. |
| 6,220,772 | B1 | 4/2001 | Taylor |

(Continued)

FOREIGN PATENT DOCUMENTS

| | | |
|---|---|---|
| WO | WO0041645 A1 | 7/2000 |
| WO | WO2004034923 A1 | 4/2004 |

(Continued)

*Primary Examiner* — Shay Karls

(57) ABSTRACT

A personal hygiene implement comprises an axle that extends along a first longitudinal axis; a movable functional element comprising a base comprising a first side and an opposing second side, a first pillar extending from the first side of the base, wherein the first pillar comprises a piston chamber that is fluidly connected to a discharging through-hole, and at least one cleaning element extending from the second side of the base; and a fixation element comprising a piston which extends orthogonally to the first longitudinal axis; wherein the movable functional element is capable of rotatably oscillating around the axle, and the piston chamber engages with the piston to form a pump.

19 Claims, 14 Drawing Sheets

(56) References Cited

U.S. PATENT DOCUMENTS

| | | |
|---|---|---|
| 6,308,367 B1 | 10/2001 | Beals et al. |
| 6,453,497 B1 | 9/2002 | Chiang et al. |
| 6,553,604 B1 | 4/2003 | Braun et al. |
| 6,564,416 B1 | 5/2003 | Claire et al. |
| 6,622,333 B1 * | 9/2003 | Rehkemper ............ A61C 17/30 15/22.1 |
| 6,826,797 B1 | 12/2004 | Chenvainu et al. |
| 6,993,804 B1 | 2/2006 | Braun et al. |
| 7,401,373 B2 | 7/2008 | Tybinkowski et al. |
| 8,356,374 B2 | 1/2013 | Castellucci |
| 8,449,295 B2 | 5/2013 | Hegemann |
| 2002/0059685 A1 | 5/2002 | Paifrath |
| 2004/0154112 A1 | 8/2004 | Braun et al. |
| 2004/0177462 A1 | 9/2004 | Brown, Jr. et al. |
| 2005/0000043 A1 | 1/2005 | Chan et al. |
| 2005/0060822 A1 | 3/2005 | Chenvainu et al. |
| 2008/0307591 A1 | 12/2008 | Farrell et al. |
| 2010/0269279 A1 | 10/2010 | Haas et al. |
| 2011/0104081 A1 | 5/2011 | Scott et al. |
| 2012/0008073 A1 | 1/2012 | Ota |

FOREIGN PATENT DOCUMENTS

| | | |
|---|---|---|
| WO | WO2007092484 A1 | 8/2007 |
| WO | WO2008135953 A1 | 11/2008 |
| WO | WO2013014617 A1 | 1/2013 |
| WO | WO2013014624 A1 | 1/2013 |

\* cited by examiner

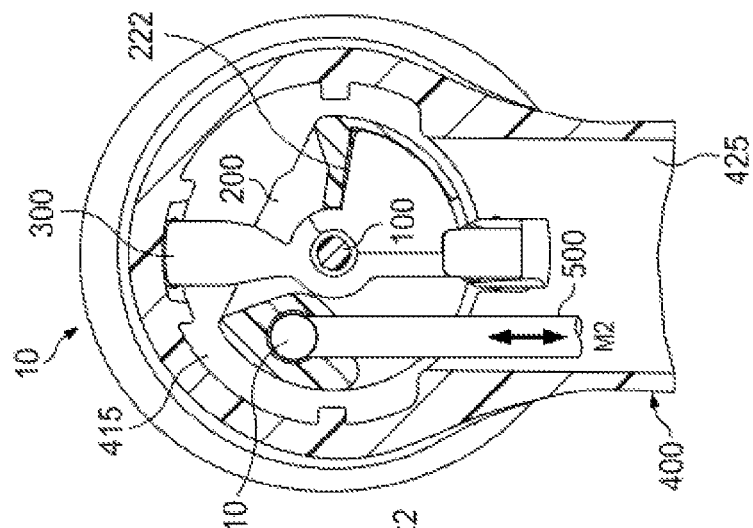
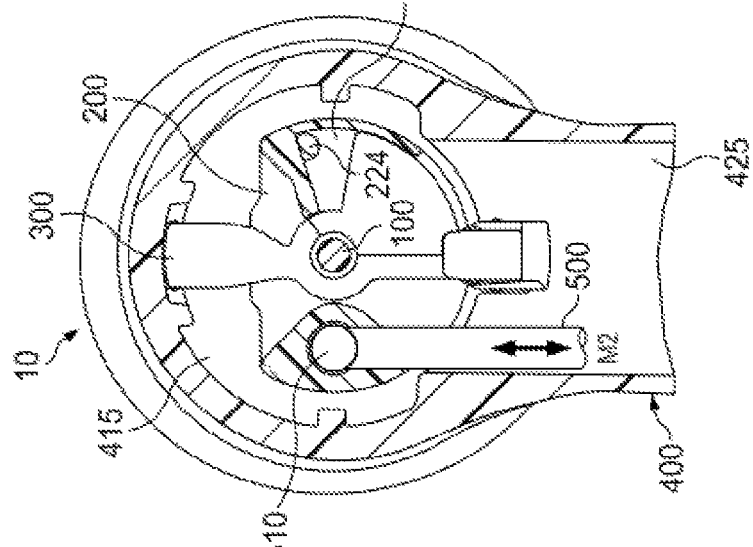
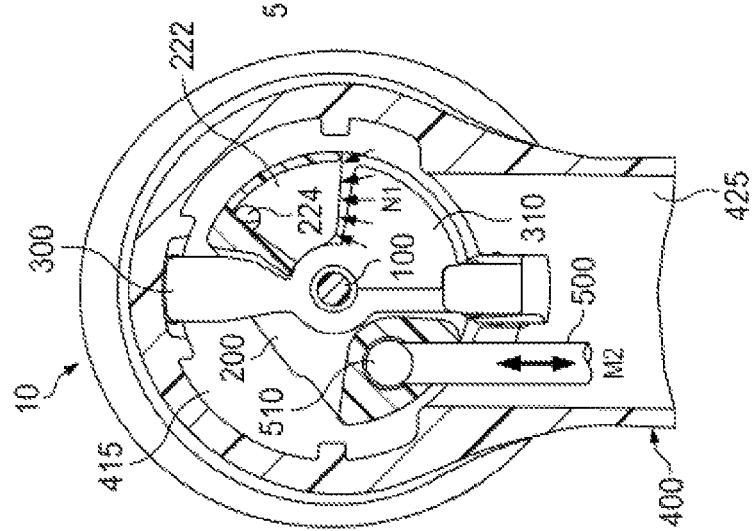

PERSONAL HYGIENE IMPLEMENT

FIELD OF THE INVENTION

The present invention is directed to a personal hygiene implement with a pump.

BACKGROUND OF THE INVENTION

Personal hygiene devices, particularly those designed for the oral cavity such as toothbrushes and oral irrigators, are well known in the art. A toothbrush generally comprises a head section mounted with tufted bristles and a handle adapted to be grasped by a user. Electric toothbrushes often have a replaceable implement containing the bristles and a handle portion containing a drive motor to drive movement of the bristles. The toothbrush is commonly used in conjunction with a dentifrice, such as toothpaste, to brush teeth. An oral irrigator, also called a dental water jet or water pick, is generally used to irrigate interdental spaces and/or tooth pockets by using a stream of pulsating water.

It has been proposed to combine the toothbrush and the oral irrigator into a single device so that teeth and interdental spaces can be cleaned effectively in one step. Attempts have been made to incorporate an oral irrigator into a toothbrush by providing a fluid conduit opening in the toothbrush head and an irrigating pump moving fluid from a cartridge to the fluid conduit opening. Many attempts require a separate drive to drive the irrigating pump. The irrigating pump is either accommodated in the toothbrush handle or as a completely external apparatus independent of the toothbrush. This typically makes the final device either expensive in construction or impracticable in operation.

Therefore, there is a need to develop an irrigating pump which is small enough to fit within a typical toothbrush for economic and practical operation. There is also a need to combine the toothbrush and the oral irrigator into a single device in a simple, reliable, and cost effective manner. It would also be advantageous, in electric toothbrush embodiments, to have both the pump and toothbrush head driven by a single drive motor.

SUMMARY OF THE INVENTION

The present invention attempts to address one or more of these needs. In one aspect, the present invention provides a personal hygiene implement, comprising:
 (a) an axle that extends along a first longitudinal axis;
 (b) a movable functional element comprising:
 (i) a base comprising a first side and an opposing second side;
 (ii) a first pillar extending from the first side of the base, wherein the first pillar comprises a piston chamber that is fluidly connected to a discharging through-hole; and
 (iii) at least one cleaning element extending from the second side of the base; and
 (c) a fixation element comprising a piston which extends orthogonally to the first longitudinal axis;
 wherein the movable functional element is capable of rotatably oscillating around the axle, and the piston chamber engages with the piston to form a pump.

In another aspect, the present invention provides a personal hygiene implement, comprising:
 (a) an axle that extends along a first longitudinal axis;
 (b) a movable functional element comprising:
 (i) a base, comprising a first side and an opposing second side;
 (ii) a first pillar extending from the first side of the base, wherein the first pillar comprises a piston which extends orthogonally to the first longitudinal axis; and
 (iii) at least one cleaning element extending from the second side of the base; and
 (c) a fixation element comprising a piston chamber that is fluidly connected to a discharging through-hole;
 wherein the movable functional element is capable of rotatably oscillating around the axle, and the piston engages with the piston chamber to form a pump.

In a further aspect, the present invention provides a personal hygiene device comprising a handle and a personal hygiene implement of the present invention that is detachably or non-detachably attached to the handle, wherein the handle comprises a drive unit to drive the movable functional element to rotatably oscillate around the axle during operation.

In yet still another aspect, the present invention provides a replacement toothbrush head, comprising:
 (a) a movable functional element comprising: either a piston or piston chamber; and preferably at least one cleaning element:
 (b) a fixation element comprising either: (i) a piston, when the movable functional element comprises a piston chamber; or (ii) a piston chamber, when the movable functional element comprises a piston;
 wherein the piston chamber engages with the piston to form a pump; and
 wherein the movable functional element is capable of oscillating, preferably rotatably oscillating around an axle, relative to the fixation element.

These and other features, aspects, and advantages of the present invention will become evident to those skilled in the art from the detailed description which follows.

BRIEF DESCRIPTION OF THE DRAWINGS

While the specification concludes with claims particularly defining and distinctly claiming the invention, it is believed that the invention will be better understood from the following description of the accompanying figures. In the accompanying figures.

FIGS. 6A to 6C are sectional top views of an exemplary personal hygiene implement of FIG. 2 with the pump in its expansion, compression, and compressed positions, respectively;

DETAILED DESCRIPTION OF THE INVENTION

Figure 1:
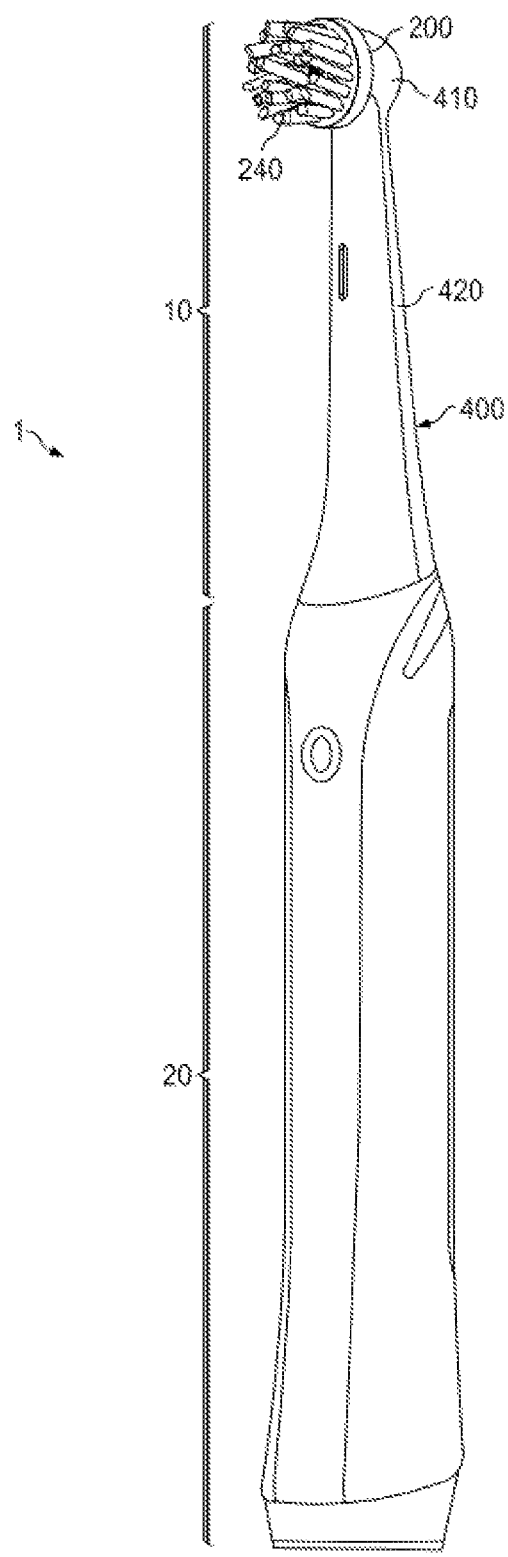
FIG. 1 is a perspective view of an exemplary personal hygiene device according to a first embodiment of the present invention.

As used herein, the articles including "a" and "an" are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

In accordance with the present invention, a personal hygiene implement comprising a "pump" is provided. The pump is formed by a piston engaging with a piston chamber. The piston is formed as part of either a movable functional element or a fixation element. In turn, the piston chamber is formed as part of either the fixation element or the movable functional element so that the fixation element and the movable functional element form a pump, i.e., a piston engaging with a piston chamber. The fixation element is fixed. In contrast, the movable functional element moves relative to the fixation element, preferably in an oscillatory movement, more preferably in a rotatably oscillatory movement around an axle and relative to the fixed fixation element. The axle extends along a first longitudinal axis. The piston and the piston chamber preferably extend orthogonally to the first longitudinal axis. In one embodiment, the piston and the piston chamber both extend in a rotational direction around the axle. The pump is actuated when the movable functional element rotatably oscillates around the axle during operation (causing the piston to engage the piston chamber). In one embodiment, the movable functional element comprises a piston chamber, and the fixation element comprises a piston. As the movable functional element oscillates (preferably rotationally oscillates), the piston of the fixation element engages the piston chamber of the movable functional element. In an alternative embodiment, the movable functional element comprises the piston, and the fixation element comprises the piston chamber.

During operation, the pump can be used to draw fluid into the piston chamber and then pump out the fluid towards a first target area. The term "fluid" is used herein in the broadest sense to include any liquid or gas or combination thereof. In one embodiment, the fluid, which may be drawn into the piston chamber, is selected from the group consisting of toothpaste slurry, saliva, air, water, mouthwash, oxygen gas, and combinations thereof. During use, toothpaste slurry, saliva, and air may be inside a user's oral cavity and may be immediately around and accessible by the pump; or water, mouthwash and oxygen gas may be contained in a fluid reservoir accommodated within or attached to the personal hygiene implement and the pump may pump the fluid from the fluid reservoir. The first target area may be any area to be cleaned or treated by the personal hygiene implement. In one embodiment, the first target area is selected from the group consisting of an oral area, a facial area, a body area, and combinations thereof. In turn, the oral area may be selected from the group consisting of tooth surface, interdental space, tooth pocket, gum line, tongue surface, and combinations thereof. The face area may be selected from the group consisting of cheek surface, nasal surface, nasal cavity, forehead surface, and combinations thereof. The body area may be selected from the group consisting of hand surface, armpit surface, foot surface, torso surface, arm surface, leg surface, and combinations thereof.

The movable functional element may further comprise at least one cleaning element for cleaning a second target area. The second target area may be selected from the group consisting of an oral area, a facial area, and a body area, and combinations thereof. The second target area may be same as or different from the first target area. For example, the first target area and the second target area may both be oral areas. In one embodiment, the first target area is interdental space while the second target area is tooth surface. When the target area is an oral area, the cleaning element may be selected from the group consisting of a bristle tuft, an elastomeric element, a movably mounted plastic element, a tongue cleaning structure, and combinations thereof. The cleaning element may be hollow or solid. Suitable examples of cleaning elements may include those described in U.S. Patent Application Publication Nos.: 2002/0059685; 2005/0000043; 2004/0177462; 2005/0060822; 2004/0154112; 2009/0007357; and U.S. Pat. Nos. 6,151,745; 6,058,541; 6,041,467; 6,553,604; 6,564,416; 6,826,797; 6,993,804; 6,453,497; 6,993,804; 6,041,467; 8,056,176. Additionally, any suitable arrangement of cleaning elements may be utilized. Non-limiting examples include those described in U.S. Pat. Nos. 5,836,769; 6,564,416; 6,308,367; 6,108,851; 6,058,541; and 5,396,678.

The personal hygiene implement of the present invention may be realized as an attachment to a handle portion of a personal hygiene device. In turn, the personal hygiene device may be selected from the group consisting of an electric toothbrush, an electric tongue scraper, an electric flossing device, an electric interdental cleaner, an electric shaver, an electric face brush or cleaner, an electric body brush or cleaner, or combinations thereof. The personal hygiene implement may be detachably or non-detachably attached to the handle portion of the personal hygiene device. The handle portion may comprise a drive unit arranged to drive the movable functional element, of the personal hygiene implement, to rotatably oscillate around an axle during operation. The drive unit may be battery operated or may be powered by a pluggable wall socket.

The following description focuses primarily on toothbrushes to further explain the present invention for the sake of convenience. These descriptions are given solely for the purpose of illustration and are not meant to be construed as limitations of the present invention, as many variations of the embodiments described hereinafter are possible without departing from the spirit and scope of the present invention.

FIG. 1 shows a perspective view of an exemplary personal hygiene device 1 according to a first embodiment of the present invention. The personal hygiene device 1 may be realized as an electric toothbrush. The personal hygiene device 1 comprises a personal hygiene implement 10 and a handle 20. The personal hygiene implement 10 may be realized as a replaceable electric toothbrush attachment which may be detachably attached to the handle 20. The personal hygiene implement 10 may comprise a movable functional element 200 and a housing 400. The movable functional element 200 may be realized as a brush head having cleaning elements 240 for cleaning teeth. The housing 400 may have a head section 410 and a neck section 420 connected to the head section 410. The movable functional element 200 may be attached to the head section 410. The neck section 420 may be attached to the handle 20. The handle 20 may comprise a drive unit (not shown) arranged to drive, during operation, the movable functional element 200 to rotatably oscillate around an axle 100 (see FIG. 2). Some suitable examples of the handle portion as well as the drive unit contained in the handle portion are disclosed, for example, in U.S. Patent Application Publication No. 2008/0307591. The housing 400, of the personal hygiene implement 10, may have an elongated, essentially tubular neck section 420 that tapers slightly from nearest the handle 20 towards the head section 410. The head section 410 may be of a generally bulbous shape. The personal hygiene implement 10 may generally be designed and dimensionalized so that at least a portion of the personal hygiene implement 10 can be placed into the oral cavity and allow for teeth cleaning of a user (including molars) while minimizing any discomfort.

Figure 2:
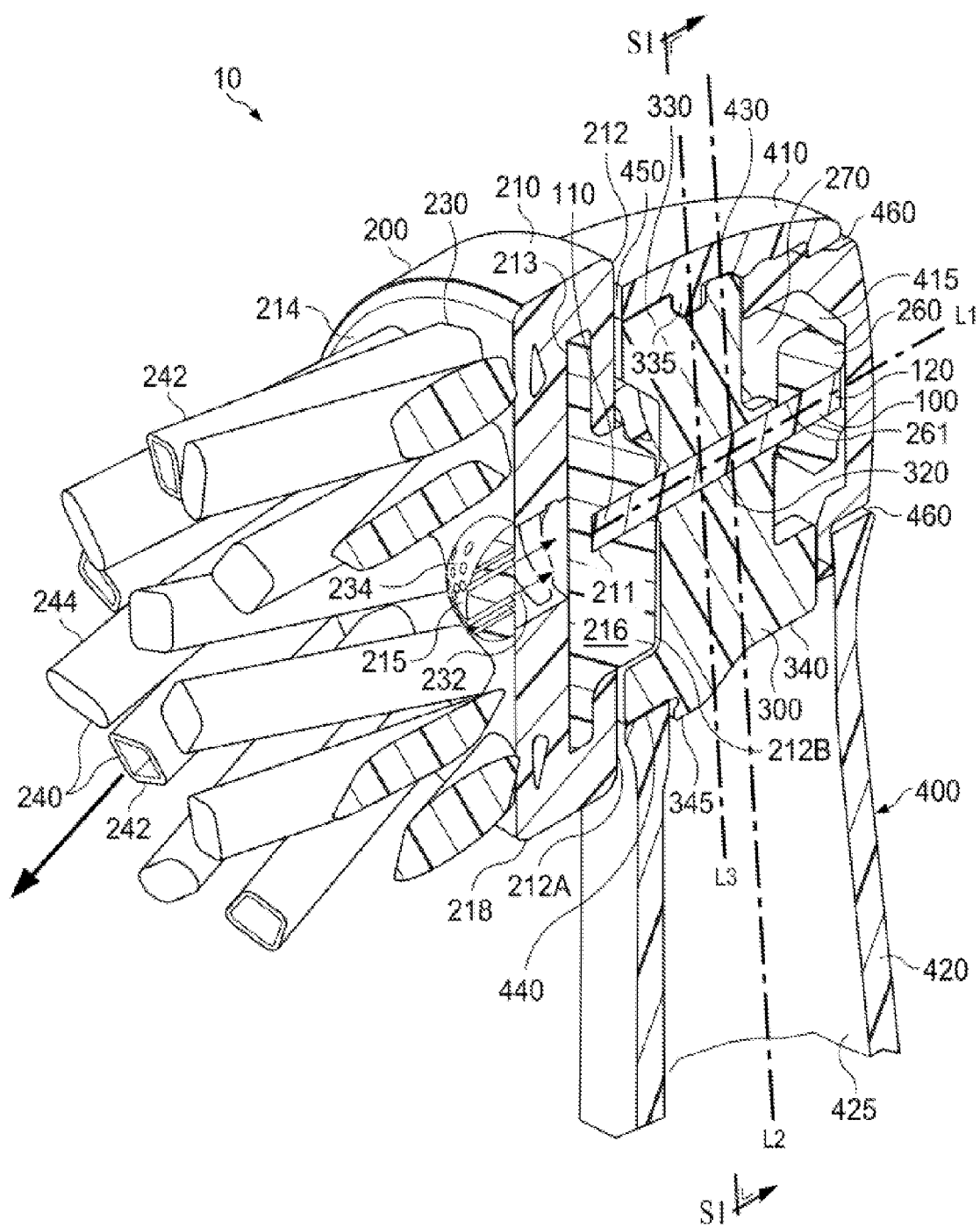
FIG. 2 is a perspective sectional view of the personal hygiene device of FIG. 1.

FIG. 2 is a perspective sectional view of an exemplary personal hygiene implement 10 of the personal hygiene device of FIG. 1. The cut plane of the sectional view of FIG. 2 goes through a first longitudinal axis L1 and a second longitudinal axis L2. L1 and L2 are orthogonal to each other. The personal hygiene implement 10 further comprises an axle 100 and a fixation element 300. The axle 100 extends along the first longitudinal axis L1, and the housing 400 extends along the second longitudinal axis L2. The head section 410 of the housing 400 has a head cavity 415 to accommodate: (i) the axle 100; (ii) the fixation element 300; and (iii) at least a part of the movable functional element 200. The fixation element 300 is fixed in the head cavity 415. The neck section 420 of the housing 400 has a neck cavity 425. The axle 100 has a first end 110 and an opposing second end 120. The axle 100 may extend through the movable functional element 200 and the fixation element 300. The axle 100 may be made of metal such as steel and/or aluminum, with a length of 0.2 cm, 0.5 cm, or 0.8 cm to 1.2 cm, 1.8 cm, or 2 cm. The movable functional element 200, the fixation element 300, and the housing 400 may be made of any suitable plastic material (such as polypropylene, polyoxymethylene, or combinations thereof) and can be injection molded.

Movable Functional Element

Still referring to FIG. 2, the movable functional element 200 comprises a base 210. The base 210 comprises a first side 212 and a second side 214. The first side 212 opposes the second side 214. The movable functional element 200 is coupled to the fixation element 300 on the first side 212. At least one cleaning element 240 extends from the second side 214 of the base 210. The base 210 may comprise an inner base 216 and an outer base 218. The inner base 216 is at least partially circumferentially surrounded by the outer base 218, and is non-detachably affixed (e.g., snapped, screwed or glued) to the outer base 218 at a base interface 213. The first side 212 may therefore comprise an outer base portion 212A and an inner base portion 212B. In an alternative embodiment, the inner base 216 and the outer base 218 may be realized as an integral element such as a plastic injection molded element. In yet alternative embodiments, the base 210 may be realized as a plurality of parts that collectively form a "base" 210 as defined herein. In a similar way, the movable functional element 200 per se may be formed integrally as one injection molded element or assembled by a plurality of parts that collectively form a "movable functional element" 200 as defined herein. Each of the parts which may be assembled together to form the movable functional element 200 may be an integral injection molded part or assembled by a plurality of sub-parts.

Figure 3A:
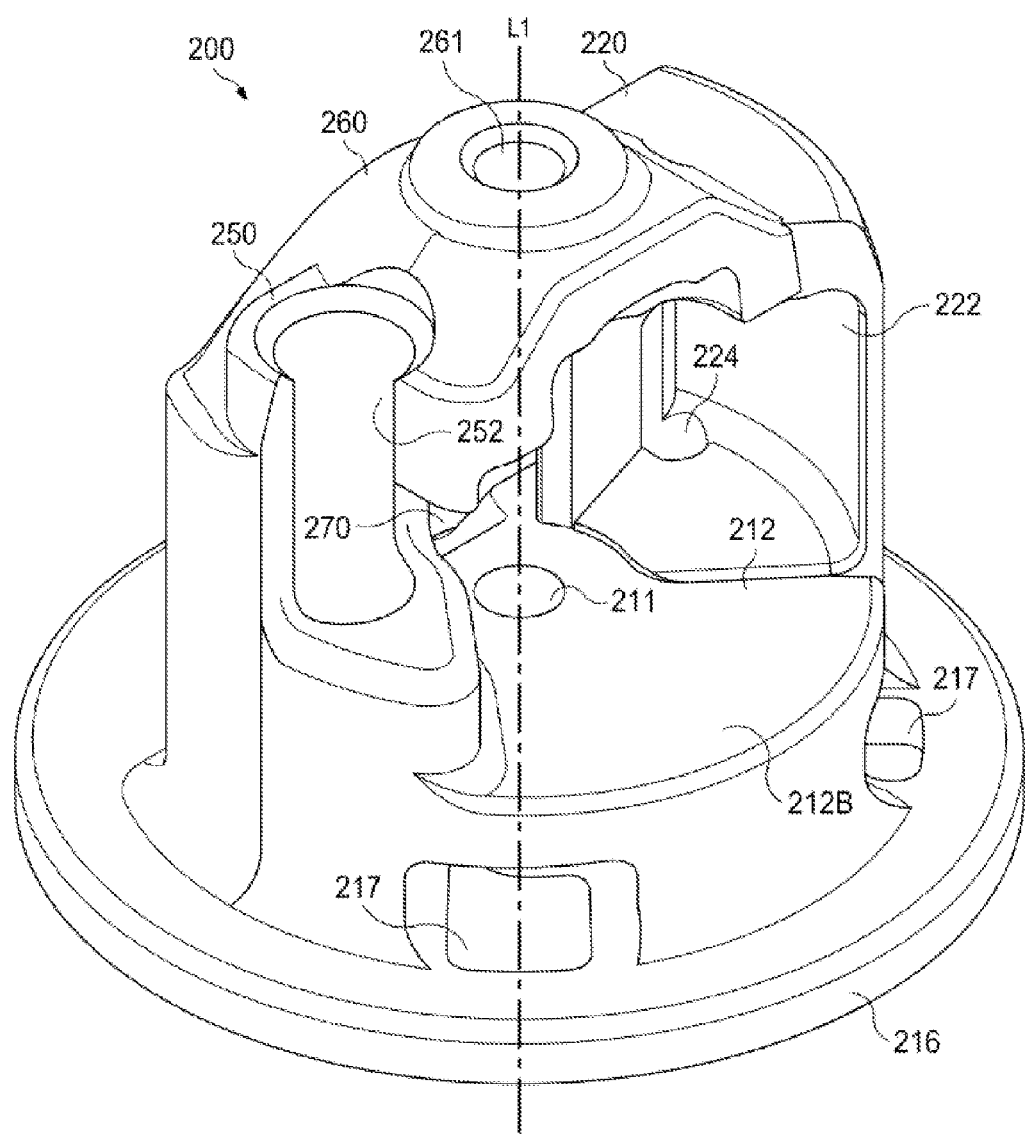
FIG. 3A is a perspective view of an exemplary movable functional element, comprising a piston chamber, of the personal hygiene implement of FIG. 2.
Figure 3B:
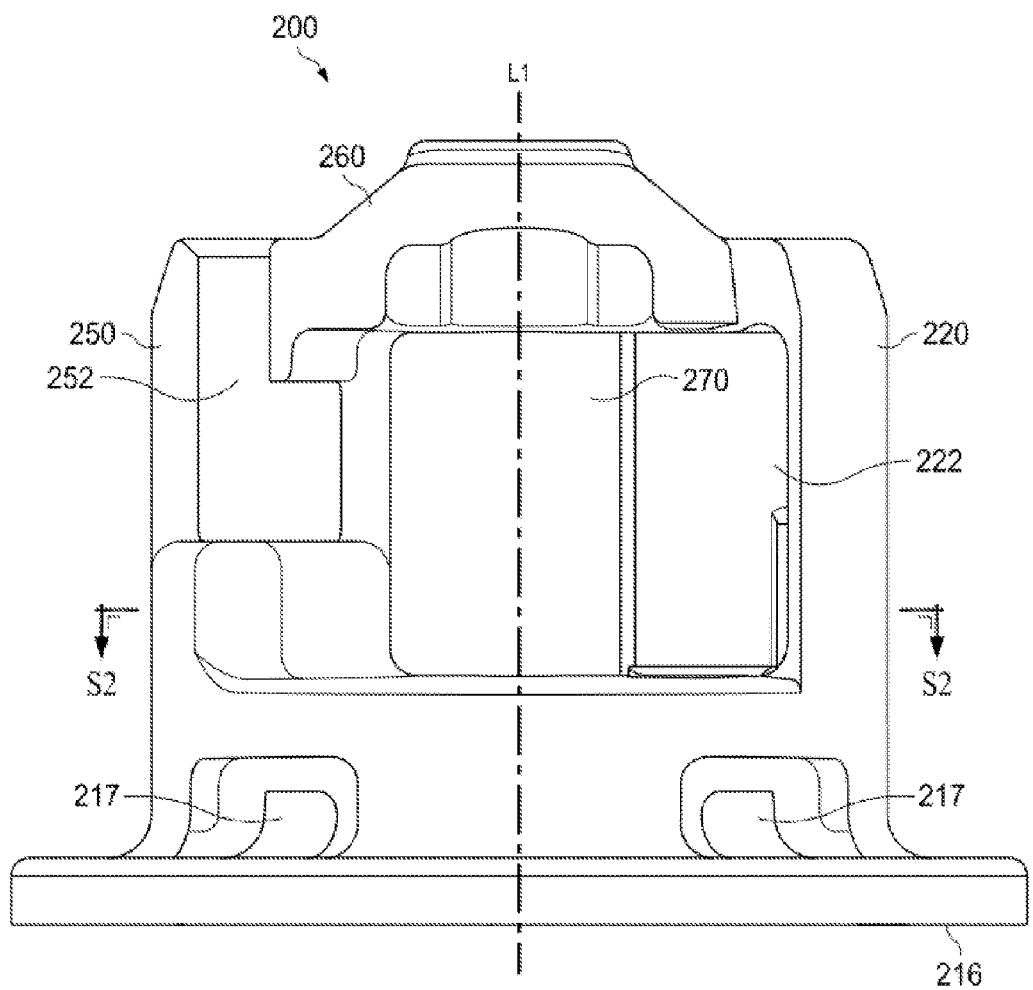
FIG. 3B is a front view of an exemplary movable functional element, comprising a piston chamber, of the personal hygiene implement of FIG. 2.
Figure 3C:
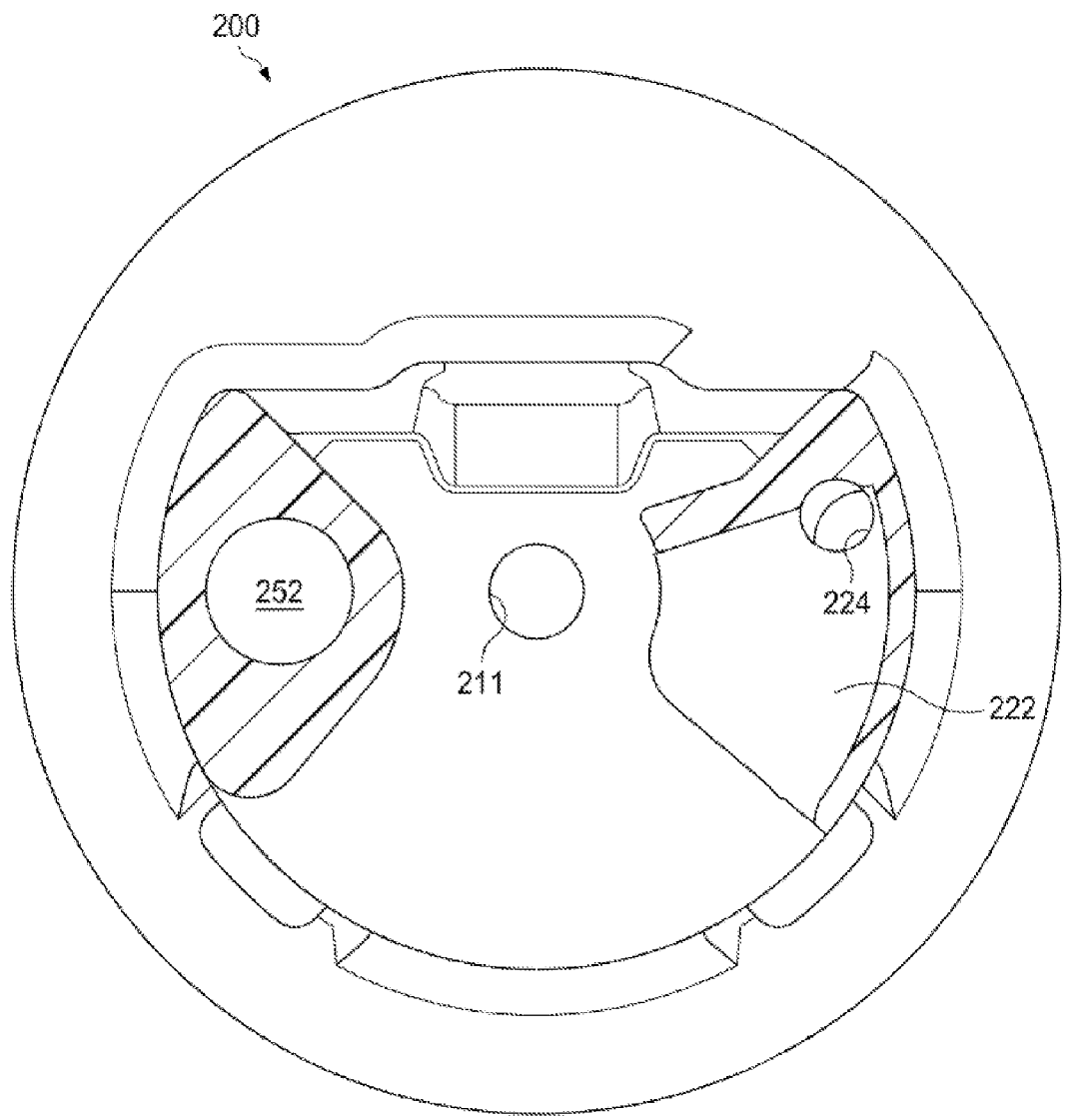
FIG. 3C is a sectional top view of an exemplary movable functional element, comprising a piston chamber, of the personal hygiene implement of FIG. 2.

The movable functional element 200 is shown in FIGS. 3A, 3B and 3C without the outer base 218 shown (for the sake of clarity). FIGS. 3A, 3B and 3C, respectively, show a perspective view, a front view, and a sectional top view. One or more connector holes 217 may be provided in the inner base 216 to connect with the outer base 218 (not shown). A first pillar 220 may extend from the first side 212 of the base 210 (wherein only the inner base portion 212B is shown). Preferably, the first pillar 220 extends parallel to the first longitudinal axis L1. The first pillar 220 comprises a piston chamber 222, wherein the piston chamber 222 has a volume from 20 mm$^3$ to 30 mm$^3$. The size of the piston chamber 222 can vary broadly, based on the size of the personal hygiene implement 10 or the desired flow rate, and other factors. In the case of a typical electric toothbrush, the piston chamber can have a volume from 1 mm$^3$, 5 mm$^3$, 10 mm$^3$, or 15 mm$^3$ to 20 mm$^3$, 30 mm$^3$, 40 mm$^3$, or 50 mm$^3$. In an alternative embodiment, the piston chamber has a volume from 5 mm$^3$ to 15 mm$^3$ or from 20 mm$^3$ to 30 mm$^3$. In the case of a typical facial brush or body brush, the piston chamber can have a volume from 10 mm$^3$, 20 mm$^3$, 30 mm$^3$, or 40 mm$^3$ to 60 mm$^3$, 70 mm$^3$, 80 mm$^3$, or 90 mm$^3$. The piston chamber 222 can be of any suitable shape. In an alternative embodiment, the first pillar 220 may comprise a piston (not shown). The piston chamber 222 or the piston (not shown) of the first pillar 220 is preferably located near the peripheral edge of the base (vs. the center) so as to take advantage of the longest traveling distance when the movable functional element 200 rotationally oscillates.

A discharging through-hole 224 is located inside the piston chamber 222 as shown in FIGS. 3A and 3C. The fluid inside the piston chamber 222 may be pumped out via the discharging through-hole 224. Referring back to FIG. 2, a plurality of cleaning elements 240 may extend from the second side 214 of the base 210. The cleaning elements 240 may comprise one or more hollow tubes 242 and one or more bristle tufts 244. One or more outlets 230, which open into the one or more hollow tubes 242 (and therefore are not clearly shown in FIG. 2) may be provided at the second side 214 of the base 210. The piston chamber 222 may be fluidly connected to the outlet 230 and the hollow tube 242 via the discharging through-hole 224. The outlet 230 and the hollow tube 242 may each independently have a cross-sectional shape selected from rectangle, round, square, triangle, T shape, U shape, L shape, or any other possible shape. In some embodiments, the outlet 230 and the hollow tube 242 may each independently have a cross-sectional area from 0.1 mm$^2$, 0.5 mm$^2$, 1 mm$^2$, or 1.5 mm$^2$ to 2.5 mm$^2$, 3 mm$^2$, 3.5 mm$^2$, or 4 mm$^2$. In an alternative embodiment, the outlet 230 and the hollow tube 242 may each independently have a cross-sectional area from 0.1 mm$^2$ to 1.5 mm$^2$ or from 2.5 mm$^2$ to 4 mm$^2$. The hollow tube 242 may have a cross-sectional shape or area same as or different from the outlet 230. Referring to FIG. 2, cleaning elements 240 extends from the second side 214 of the base 210. The cleaning elements 240 may comprise a plurality of hollow tubes 242 and a plurality of bristle tufts 244. One or more of the outlets 230 may open into the hollow tubes 242. The bristle tufts 244 may be mounted by anchor tufting technology on the second side 214 of the base 210. The hollow tubes 242 may be realized as elastomeric elements made of any suitable material such as a flexible material selected from the group consisting of polypropylene, thermoplastic elastomer, polyoxymethlylene, a blend of polyester and polycarbonate, acrylonitrile styrene acrylateor, polybutylene terephthalate, and combinations thereof. The hollow tubes 242 may have any suitable height (i.e., longest dimension), preferably from 0.2 mm, 2 mm, 5 mm, or 10 mm to 15 mm, 20 mm, 25 mm, or 30 mm in height. The hollow tube 242 may have a cross sectional shape or area same as or different from the outlet 230. The hollow tube 242 may be tapering along the height dimension (in either direction). In some embodiments, the hollow tube 242 extends from the second side 214 of the base 210 with an inclination angle, preferably from 10°, 20°, 30°, or 40° to 60°, 70°, 80°, or 90°, with respect to the second side 214 of the base 210. In an alternative embodiment, only one outlet 230 opening up into one hollow tube 242 are provided on the second side 214 of the base 210. The bristle tufts 244 may be mounted by anchor tufting technology on the second side 214 of the base 210. The height of the bristle tufts 244 may be same as or different from the height of the hollow tubes 242.

As best illustrated in FIG. 3A, the movable functional element 200 may further comprise a second pillar 250 and a bridge 260. The second pillar 250 may protrude from the inner base portion 212B of the first side 212 and is connected with the first pillar 220 by the bridge 260 to define an opening 270. The first pillar 220, the second pillar 250 and the bridge 260 may be arranged such that the axle 100 traverses the opening 270. The opening 270 may have a length of 0.1 cm, 0.3 cm, or 0.5 cm to 0.8 cm, 1.2 cm, or 1.5 cm along the first longitudinal axis L1. The second pillar 250 may extend parallel to the first pillar 220. The second pillar 250 may be located at the farthest distance from the first pillar 220 on the inner base portion 212B of the first side 212. The bridge 260 may have a length of 0.2 cm, 0.5 cm, or 0.8 cm to 1.2 cm, 1.8 cm, or 2 cm (measured orthogonally to the first longitudinal axis L1).

Still referring to FIG. 3A, the movable functional element 200 may have a first bore 211 and a second bore 261 that extend along the first longitudinal axis L1 and support the axle 100. The first bore 211 may be provided in the first side 212 of the base 210 of the movable functional element 200. The first bore 211 may go into the inner base 216 but does not intersect the outer base 218. The second bore 261 may be provided in the bridge 260. The axle 100 may be affixed to the movable functional element 200 by the first bore 211 and the second bore 261. It is particularly advantageous that the axle 100 is affixed to the first bore 211 and the second bore 261 of the movable functional element 200. In particular, the first bore 211 and the second bore 261 are arranged on opposing sides of the opening 270 along the first longitudinal axis L1, and have a relatively large distance between each other. This likely leads to a reduction of wobbling the movable functional element 200 may experience during operation (i.e., when the movable functional element 200 rotates and/or oscillates around the first longitudinal axis L1) in comparison to embodiments in which the axle 100 traverses a single bore at a single location in the movable functional element 200. This is particular relevant when the movable functional element 200 is driven to a high-frequency oscillation (e.g. an oscillation frequency above 80 Hz, above 90 Hz, above 100 Hz, above 110 Hz, above 120 Hz, above 130 Hz, above 140 Hz, or even above 150 Hz). The oscillation frequency of the movable functional element 200 is generally no greater than 300 Hz.

Referring to FIG. 2, the axle 100 has a first end 110 and an opposing second end 120. The axle 100 extends through the movable functional element 200. The first end 110 of the axle 100 is affixed to the first side 212 by the first bore 211. The second end 120 of the axle 100 is affixed to the bridge 260 by the second bore 261.

The movable functional element 200 may have a shaft cavity 252 to receive a shaft element 500 (as shown in FIGS. 6A, 6B and 6C). The shaft element 500 is capable of engaging with a drive unit (not shown) to drive the movable functional element 200 into motion around the axle 100 during operation. The shaft cavity 252 may extend into at least a portion of the bridge 260 and/or the second pillar 250. In a specific embodiment, the shaft cavity 252 may extend through the bridge 260 and into the second pillar 250. The shaft cavity 252 may be of a cylindrical shape and the longitudinal axis of the cylinder may be parallel with the first longitudinal axis L1. FIG. 3C is a sectional top view of the movable functional element 200 cut through a plane S2 which is orthogonal to the first longitudinal axis L1 as shown in FIGS. 3A and 3B. As shown in FIG. 3C, the shaft cavity 252 may be provided at the farthest distance from the piston chamber 222 on the inner base portion 212B of the first side 212 of the base 210.

Fixation Element

Referring back to FIG. 2, the fixation element 300 may be affixed inside the head cavity 415 of the housing 400. The fixation element 300 may be elongated and extend along a third longitudinal axis L3, wherein the third longitudinal axis L3 is orthogonal to the first longitudinal axis L1.

The fixation element 300 can be affixed at one or more locations within the head section 410 so that the fixation element 300 is in a fixed relationship to the movable functional element 200. In some embodiments, the fixation element 300 is affixed at least at two different locations (not shown) of the head section 410, wherein these locations are essentially opposingly arranged. In some embodiments, the fixation element 300 is non-detachably affixed inside the head cavity 415. In some embodiments, the fixation element 300 extends in a curved manner between two affixation locations. The fixation element 300 may have a first fixation element end 330 and a second fixation element end 340 that are opposing each other. The first fixation element end 330 may comprise a first snap-nose 335. The second fixation element end 340 may comprise a second snap-nose 345. The first snap-nose 335 may be snapped into a first recess 430 in the head section 410 of the housing 400 of the oral hygiene implement 10, and the second snap-nose 345 may be snapped into a second recess 440 in the head section 410 of the housing 400. These snap connections may be non-detachable such that the mounted fixation element 300 cannot be readily separated from the head section 410. The first snap-nose 335 and the second snap-nose 345 of the fixation element 300 may have 90 degree undercuts that extend into the first recess 430 and the second recess 440 provided in the head section 410. Such an arrangement prevents the fixation element 300 from being easily separated from the head section 410 when mounted. In an alternative embodiment, the fixation element 300 may be glued or screwed or welded to the head section 410 of the housing 400, or otherwise fixedly secured to the head section 410. In another alternative embodiment, the fixation element 300 and the housing 400 may be realized as an integral element. In another alternative embodiment, the fixation element 300 may be detachably secured at the housing 400, where the threshold force to detach the fixation element 300 from the housing 400 is chosen so high that the fixation element 300 will not be unintentionally detached during regular use of the oral hygiene implement 10.

Figure 4A:
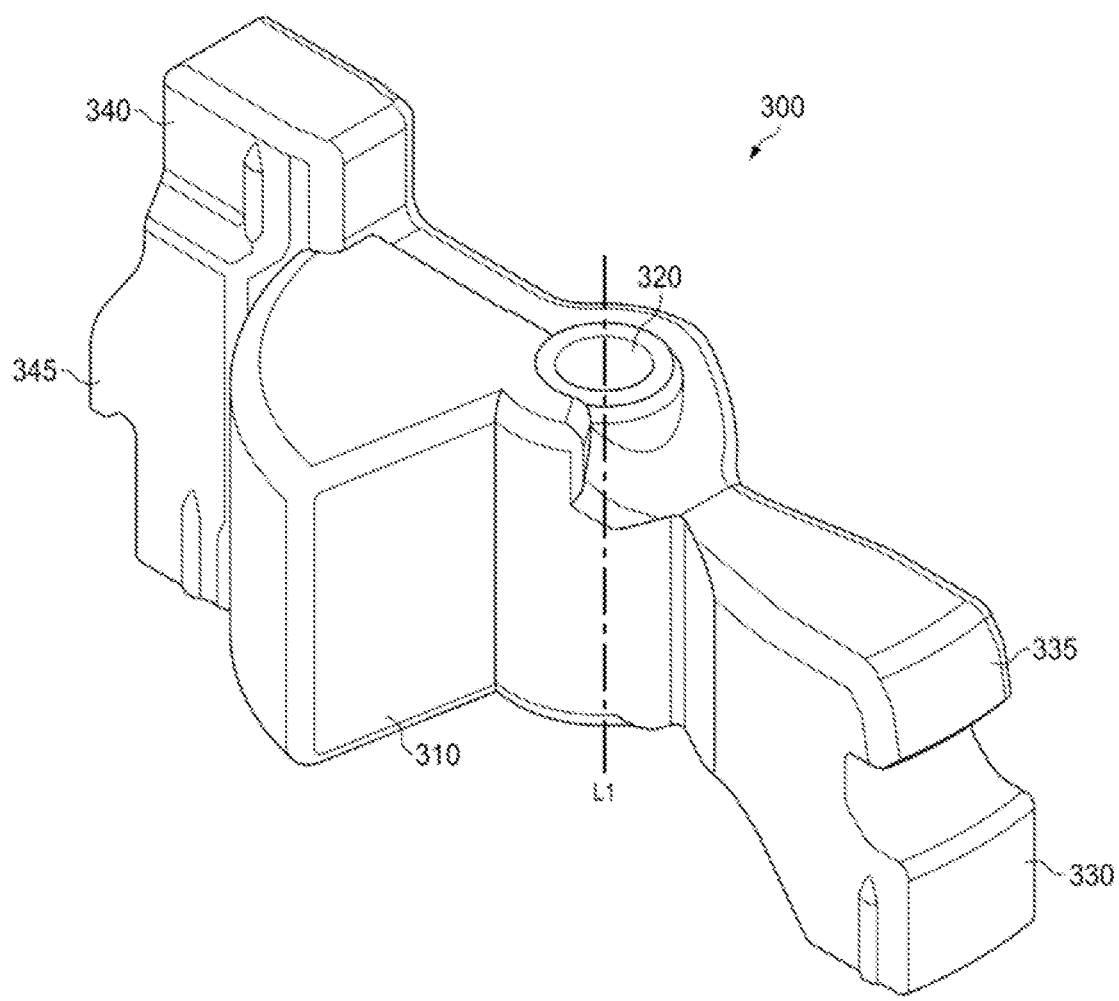
FIG. 4A is a perspective view of an exemplary fixation element, comprising a piston, of the personal hygiene implement of FIG. 2.
Figure 4B:
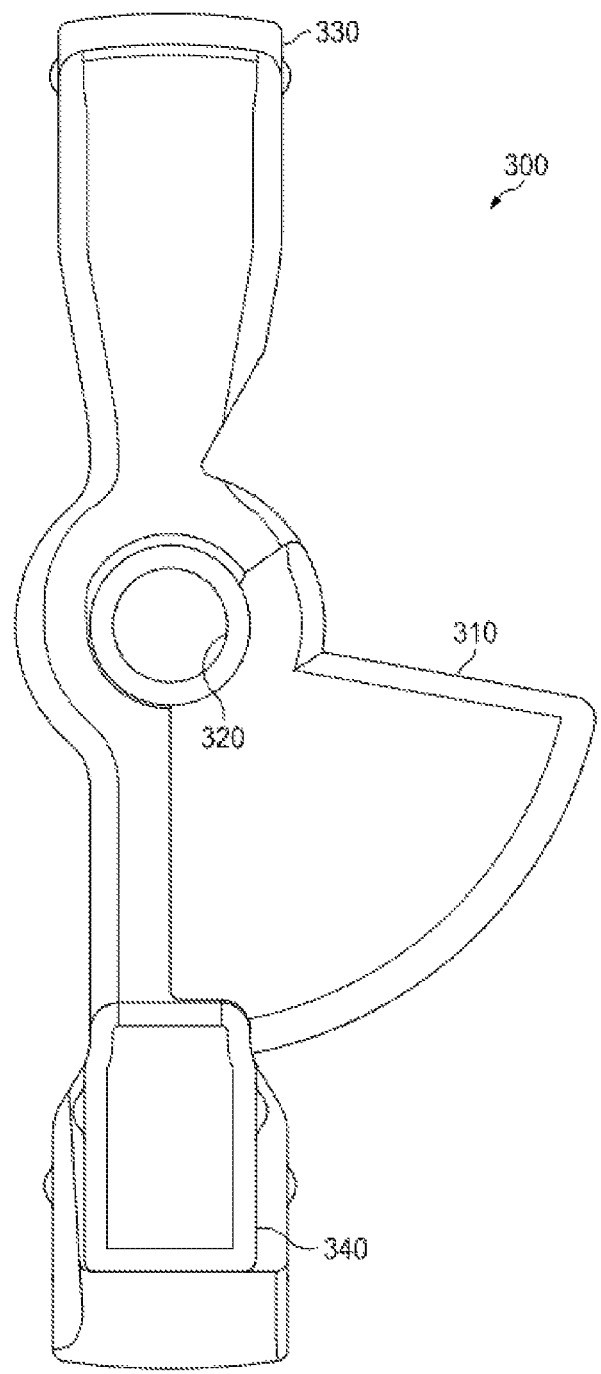
FIG. 4B is a top view of an exemplary fixation element, comprising a piston, of the personal hygiene implement of FIG. 2.

FIGS. 4A and 4B are, respectively, a perspective view and a top view of the fixation element 300. As shown in FIGS. 4A and 4B, the fixation element 300 comprises a piston 310. The piston 310 is designed to engage the piston chamber 222 (as shown in FIGS. 3A to 3C) so as to occupy or substantially occupy the volume of the piston chamber 222. Accordingly, the dimensions of the piston 310 will essentially mirror the volume of the piston chamber 222 but slightly less so as to allow the piston 310 to engage the piston chamber 222 (i.e., allow the piston 310 to be received within the piston chamber 222). In an alternative embodiment when the movable functional element 200 comprises a piston (not shown), the fixation element 300 may comprise a piston chamber (not shown). The fixation element 300 may have a third bore 320, extending along the first longitudinal axis L1. The axle 100 may extend through the fixation element 300 and be bored into the third bore 320, as shown in FIG. 2.

Referring to FIG. 2, the fixation element 300 may extend at least partially through the opening 270, preferably entirely through the opening 270 such that the bridge 260 transverses the middle of the fixation element 300. This arrangement permits the movable functional element 200 and the fixation element 300 to engage each other in a sustained and reliable fashion, reducing or even eliminating side-to-side movements during operation which might otherwise cause dysfunction of the pump—particularly at higher oscillation frequencies. The fixation element 300 may traverse through the opening 270 of the movable functional element 200 such that the axle 100 in turn traverses through the fixation element 300, preferably goes through the center of the fixation element 300. With this arrangement, the movable functional element 200 may be non-detachably fixed to the fixation element 300 (and in a rotational relationship thereof). Such an arrangement is advantageous in that the fixation element 300 locks the movable functional element 200 with respect to the head section 410 of the housing 400. Since the fixation element 300 may in particular be non-detachably fixed at the housing 400, and the movable functional element 200 is non-detachably fixed to the fixation element 300, any extreme force excreted during regular use of the oral hygiene implement 10 will not lead to a separation of the movable functional element 200 from the housing 400. Such an arrangement also ensures a reliable engagement between the piston chamber 222 and the piston 310 in the operation of the pump.

Pump

Figure 5A:
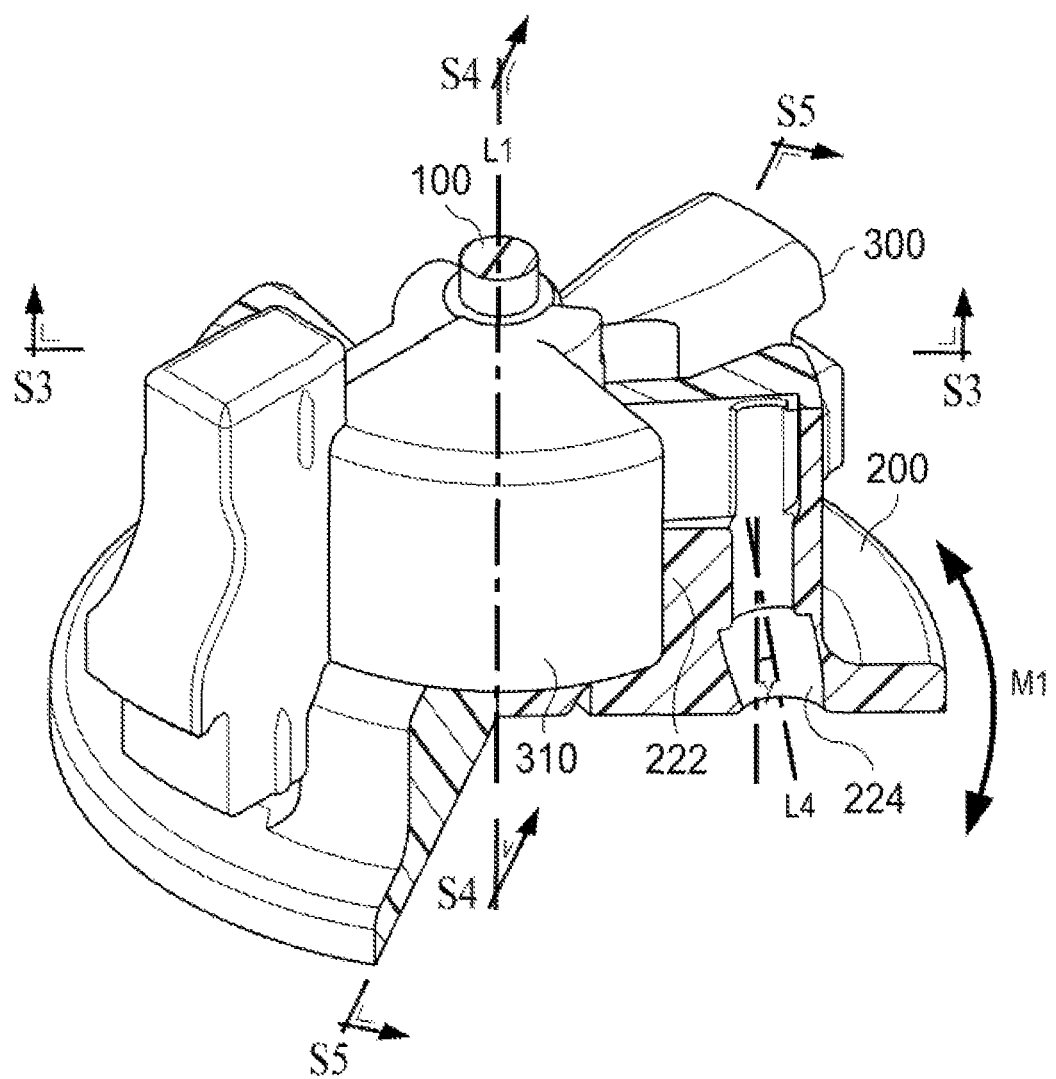
FIGS. 5A and 5B are sectional perspective views of an exemplary pump of the personal hygiene implement of FIG. 2, with the piston out of the piston chamber and inside the piston chamber, respectively.
Figure 5B:
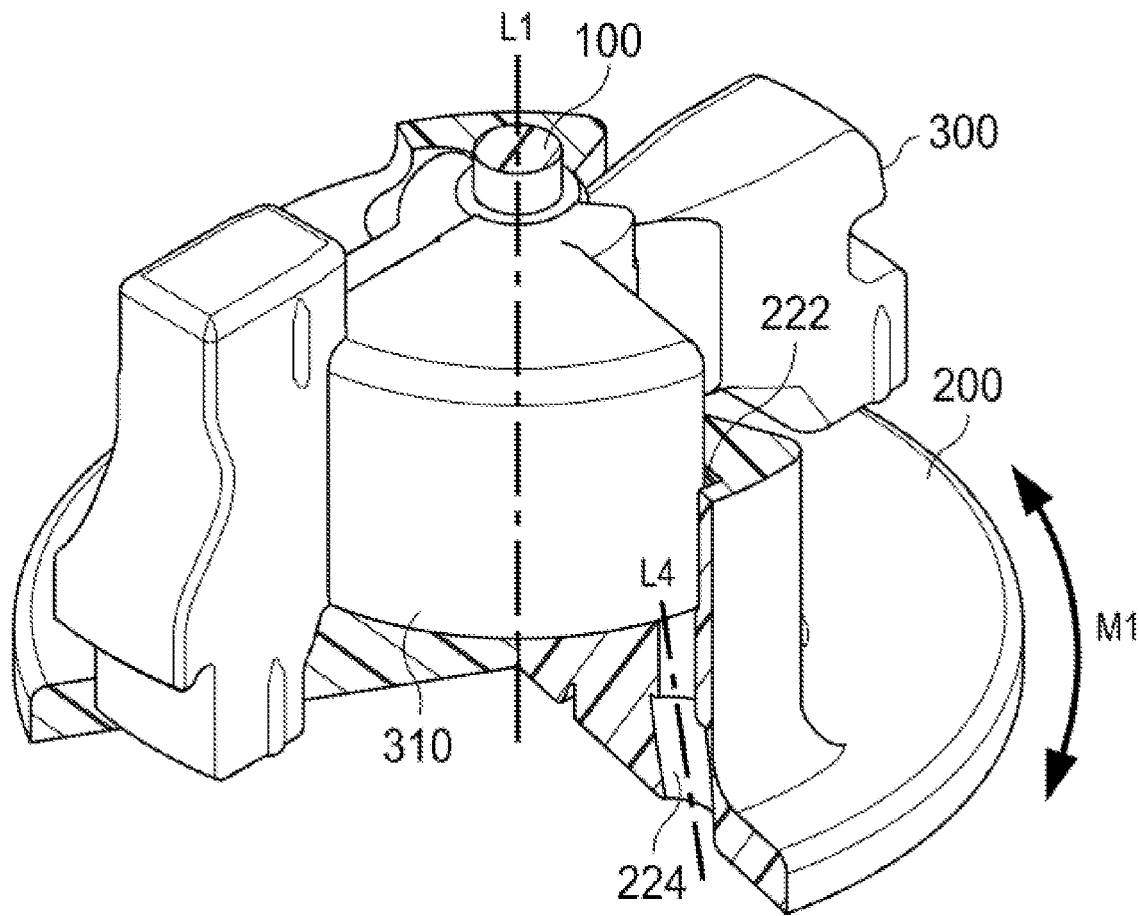

FIGS. 5A and 5B are sectional perspective views showing how the axle 100, the movable functional element 200, and the fixation element 300 are assembled together to form the pump. In these figures, the movable functional element 200 is shown without the outer base 218 for the sake of clarity, and is cut through three cut planes S3, S4 and S5. The cut plane S3 horizontally traverses (i.e., orthogonally to L1) the first pillar 220, the axle 100, and the second pillar 250, removing the bridge 260 so as to expose the fixation element 300. The cut plane S4 vertically extends from the axle 100 and cuts the discharging through-hole 224 halfway open. The cut plane S5 vertically extends from the axle 100 and forms a 90 degree angle with the cut plane S4. The cut plane S4 and the cut plane S5 together make a 90 degree slice missing from the movable functional element 200 so as to expose the cut-open discharging through-hole 224. No cut is made to the fixation element 300.

FIG. 5A shows the pump in an "open position" with the piston 310 outside of the piston chamber 222. FIG. 5B shows the pump in a "closed position" with the piston 310 inside the piston chamber 222. The movable functional element 200 is capable of rotatably oscillating around the axle 100, as shown by a double arrow M1. The piston 310 and the piston chamber 222 extend along the rotational direction M1 around the axle 100. For example, the piston 310 may be a "pie-slice" of 45 degree to 90 degree around the axle 100, and the piston chamber 222 essentially mirrors the shape of the piston 310 so as to receive the piston 310 during operation. When the movable functional element 200 is oscillating rotationally around the axle 100, the piston 310 goes inside and outside of the piston chamber 222 to make the pump work. When the relative position of the movable functional element 200 and the fixation element 300 removes the piston 310 from the piston chamber 222 (i.e., when the pump is in the open position), fluid immediately around the piston chamber 222 can be drawn therein due to a negative pressure created in the piston chamber 222. When the movable functional element 200 rotates around the axle 100 to insert the piston 310 inside the piston chamber 222 (i.e., when the pump is in the close position), the fluid contained in the piston chamber 222 is compressed out of the piston chamber 222 via the discharging through-hole 224 and is ultimately directed to the first target surface by the outlets 230 and the hollow tubes 242 (see FIG. 2). In an embodiment, the movable functional element 200 may have a rotational degree of freedom around the axle 100 from 10, 20, 30 or 40 degrees to 60, 70, 80, or 90 degrees. In an alternative embodiment, the movable functional element 200 may have a rotational degree of freedom around the axle 100 from 10 degrees to 40 degrees or from 60 degrees to 90 degrees.

As shown in FIG. 5A, the discharging through-hole 224 extends linearly along a fourth longitudinal axis L4 and exits through the outlet 230 (see FIG. 2). In an embodiment, the fourth longitudinal axis L4 is angled with respect to the first longitudinal axis L1 by an angle γ. The angle γ is preferably from 2°, 5°, 8°, or 10° to 15°, 20°, 25°, or 30°. In yet another embodiment, although not shown, L4 is parallel with L1 (i.e., γ is 0°). The discharging through-hole 224 has a cross sectional area (along a direction orthogonal to the fourth longitudinal axis L4) from $0.3 \text{ mm}^2$, $0.5 \text{ mm}^2$, or $0.8 \text{ mm}^2$ to $1.5 \text{ mm}^2$, $2.0 \text{ mm}^2$, or $2.5 \text{ mm}^2$. By properly designing the angle γ and the cross sectional area of the discharging through-hole 224, a "backflow" through the discharging through-hole 224 when there is a negative pressure in the piston chamber 222 can be prohibited and no check valve or similar device is needed to avoid the "backflow". This significantly reduces the manufacture and maintenance costs of the pump. The discharging through-hole 224 may be of a cylindrical shape and have a length of 0.05 cm, 0.1 cm, or 0.2 cm to 0.4 cm, 0.5 cm, or 0.7 cm along the fourth longitudinal axis L4.

FIGS. 6A, 6B, and 6C are three sectional top views of the personal hygiene implement 10 showing three different steps during a single rotary oscillation cycle. The movable functional element 200 and the housing 400 are cut through a plane S1 to expose the fixation element 300 and the shaft element 500. As shown in FIG. 2, the plane S1 is orthogonal to the first longitudinal axis L1 and parallel with the second longitudinal axis L2. The neck cavity 425 of the housing 400 may be essentially hollow and accommodate a shaft element 500 that may be realized as a push rod. The shaft element 500 may extend through the neck cavity 425 into the head cavity 415 of the housing 400. The shaft element 500 may comprise a pivot pin 510 that is capable of fitting into the shaft cavity 252. The shaft element 500 may be coupled to the movable functional element 200 by means of the pivot pin 510 received into the shaft cavity 252. When the shaft element 500 is driven to linearly oscillate along its longitudinal extension direction as indicated by a double arrow M2, the pivot pin 510 induces an oscillating rotation of the movable functional element 200 around the axle 100. The pivot pin 510 can freely rotate in the shaft cavity 252 so that the shaft element 500 is not bent when it linearly oscillates. The peak amplitude value of the linear oscillation of the shaft element 500 may be from ±0.1 mm, ±0.2 mm, or ±0.3 mm to ±0.5 mm, ±0.8 mm, or ±1.0 mm. The movable functional element 200 may therefore oscillate rotationally around the axle 100 with a peak oscillation angle from 10, 20, or 30 degrees to 50, 70, or 90 degrees. The oscillation frequency of the shaft element 500 and the movable functional element 200 may be above 100 Hz, for example, from 110 Hz, 130 Hz, 150 Hz, or 170 Hz to 190 Hz, 210 Hz, 230 Hz, or 250 Hz. In a specific embodiment, the movable functional element 200 is driven to oscillate with an oscillation frequency from 150 Hz to 250 Hz and a peak oscillation angle from 30 degrees to 50 degrees during operation.

By the rotary oscillation movement of the movable functional element 200, the piston 310 goes inside and outside the piston chamber 222. When the shaft element 500 is in its lowest position (of a rotary oscillation cycle) as shown in FIG. 6A, the piston 310 is outside of the piston chamber 222. A negative pressure is built up inside the piston chamber 222, and the fluid immediately around the piston chamber 222 is drawn into the piston chamber 222 as indicated by the arrows N1. When the shaft element 500 goes to a central position (during a rotary oscillation cycle) as shown in FIG. 6B, a positive pressure is created in the piston chamber 222, and the fluid inside the piston chamber 222 is pushed out through the discharging through-hole 224 towards the outlet 230 and the hollow tube 242 (as shown in FIG. 2). Finally, when the shaft element 500 goes to its highest position as shown in FIG. 6C, the piston 310 compresses almost all the fluid out of the piston chamber 222 and then the next rotary oscillation cycle is initiated once the shaft element 500 returns back to its lowest position as shown in FIG. 6A.

The fluid pumped out of the piston chamber 222 can improve the cleaning of the gum pockets and can flush the spaces between the teeth (and other hard to reach areas by typical brushes). The working mechanism of the present invention is similar to the function of an oral irrigator. According to a specific embodiment of the present invention, the pumped fluid may have a flow rate up to 8.4 ml/min and may spray up to 1.5 m high.

Since the head cavity 415 is not fluid tight, fluid can easily go into the head cavity and therefore surround the pump, enter the piston chamber 222 and subsequently be pumped. For example, the fluid can go into the head cavity through the fit clearance 450 between the base 210 of the movable functional element 200 and the head section 410 of the housing 400. The head section 410 of the housing 400 may further comprise a cutout 460 (see FIG. 2), which for example, is located farthest away from the base 210 along the first longitudinal axis L1. The cutout 460 can also allow fluid to go into the head cavity 415.

In one embodiment, an inlet may be provided. As shown in FIG. 2, an inlet 232 may be provided in the center 215 of the second side 214 of the base 210 of the movable functional element 200 and in fluid communication with the piston chamber 222. The center 215 of the second side 214 traverses the first longitudinal axis L1. The cleaning elements 240 are arranged on the second side 214 by generally leaving the area immediately nearest the inlet 232 devoid of cleaning elements 240. During operation, a negative pressure can be formed around the inlet 232, making it possible to draw fluid into the piston chamber 222 through the inlet 232.

The arrangement of multiple hollow tubes 242 on the second side 214 but away from the center 215 of the second side 214 as shown in FIG. 2 can further increase the negative pressure around the inlet 232. A further advantage of this arrangement is that the negative pressure around the inlet 232 not only draws the fluid into the piston chamber 222, but may also draw dirt or loosens plaque away from the teeth during operation.

A filter 234 can be disposed in fluid communication with the piston chamber. The filter 234 may be provided upstream of the inlet 232 to prevent the dirt or the plaque from going into the piston chamber 222 during pump operation. Additionally or alternatively, a filter may also be provided downstream of the inlet 232 or pump but upstream of the outlet 230, to purify, sterilize or clean the fluid before it is pumped out to the first target surface. The filter 234 may comprise a metal material, preferably a metal catalyst. The metal material may be selected from the group consisting of silver, copper, gold, rhodium, platinum, palladium, and combinations thereof. It may be possible to create an "oxygen flush" by decomposing hydrogen peroxide with such metal material (e.g. silver). By carrying oxygen to the gum pockets or the interdental space, bacteria could be killed or inhibited. The hydrogen peroxide can be delivered to the oral cavity in a dentifrice (mixing with saliva to become a pumpable fluid). In some embodiments, the metal material may be disposed in fluid communication with the piston chamber in any form other than a filter.

Liquid and air may be received as a fluid by the pump and mixed together during the pumping action resulting in a foamed spray. The foam parameters can be controlled, at least in part, by the design and dimensions of the discharging through-hole 224, the outlet 230, and/or the hollow tube 242. Some foaming ingredients may be included in a dentifrice (used in conjunction with the toothbrush) to facilitate foaming, for example, those disclosed in U.S. Patent Application Publication Nos. 2006/110516A1 and 2002/187234A1, as well as in U.S. Pat. No. 6,713,113 B2.

Figure 7:
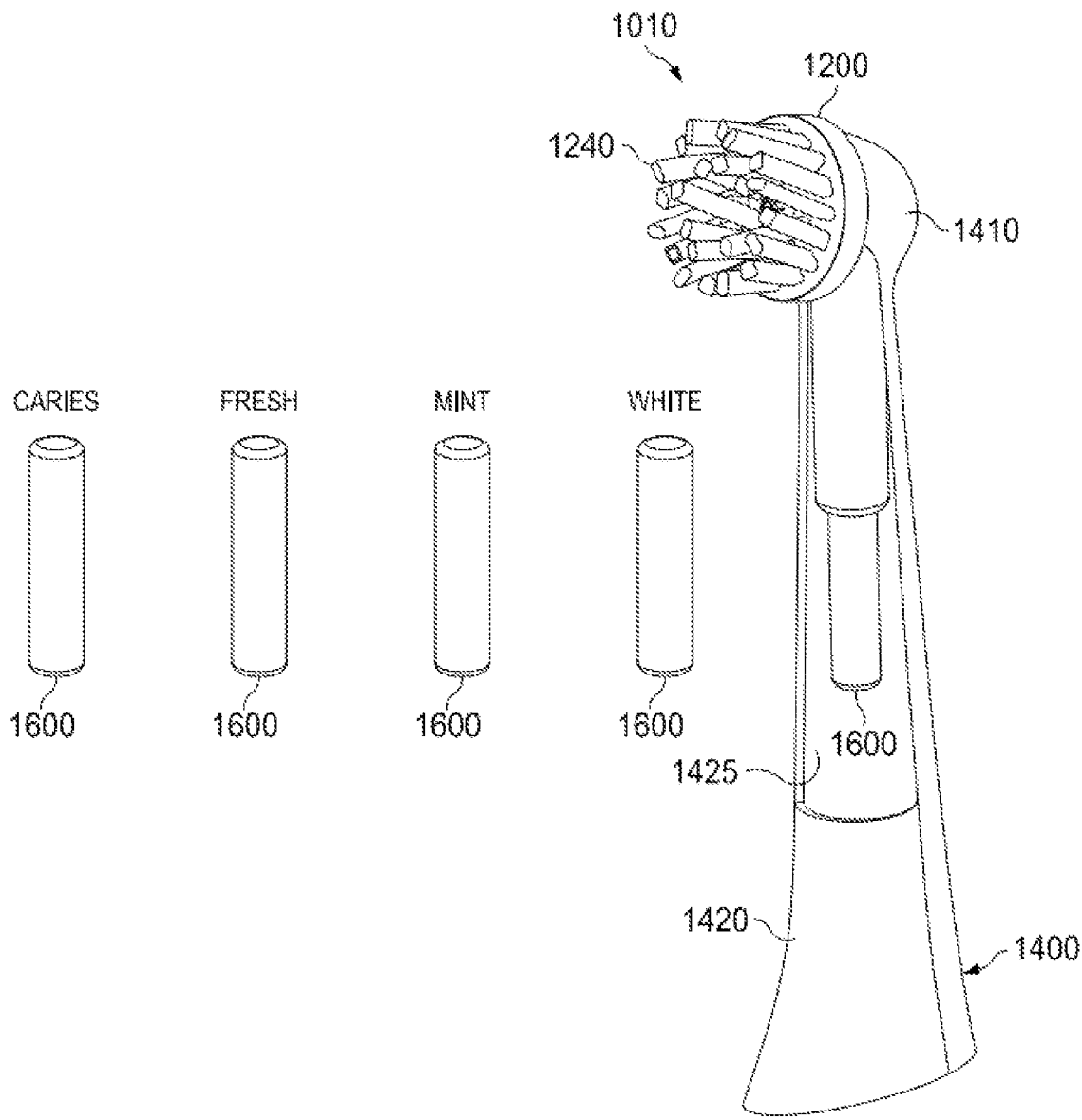
FIG. 7 is a perspective view of an exemplary personal hygiene implement comprising a reservoir according to a second embodiment of the present invention.

FIG. 7 shows a perspective view of an exemplary personal hygiene implement 1010 which comprises a reservoir 1600, according to a second embodiment of the present invention. The personal hygiene implement 1010 comprises a movable functional element 1200 and a housing 1400. The movable functional element 1200 is realized as a brush head having cleaning elements 1240 for cleaning teeth. The housing 1400 has a head section 1410 and a neck section 1420 connected to the head section 1410. The movable functional element 1200 is attached to the head section 1410. The neck section 1420 may be attached to a handle (not shown). The neck section 1420 has a neck cavity 1425. The reservoir 1600 may be contained in the neck cavity 1425. The reservoir 1600 may be refillable or disposable or replaceable or combination thereof. The reservoir 1600 may contain a liquid fluid and/or a gas fluid. The reservoir 1600 may be realized as various cartridges which can be installed much like ink cartridges of a writing pen. The user can choose among different cartridges depending on desired oral care requirements. Various cartridges can be selected for a single oral care event or a single cartridge can be used for multiple oral care events. For example, the user could insert a freshening cartridge in the morning of a first day and a tooth whitening cartridge in the evening of the same day or in the morning of a second day. The reservoir 1600 may be for a single dose use. In other words, the reservoir 1600 may be emptied/refilled after only a single brushing event. Alternatively, the reservoir 1600 may be designed for a plurality of doses. The reservoir 1600 may be used to provide additional benefits by providing specific actives, such as whitening or bleaching agents, anti-caries agents, antibacterial agents, local or systemic antibiotics, and so on. The benefits may compliment or be synergistic to dentifrice or other oral care composition/treatment regimens. Non-limiting examples of these actives include those described in US 2011/0104081 A1 at paragraphs 55 to 65, as well as the references cited therein. In an alternative embodiment, the reservoir may be contained in a handle portion of a personal hygiene implement.

Figure 8A:
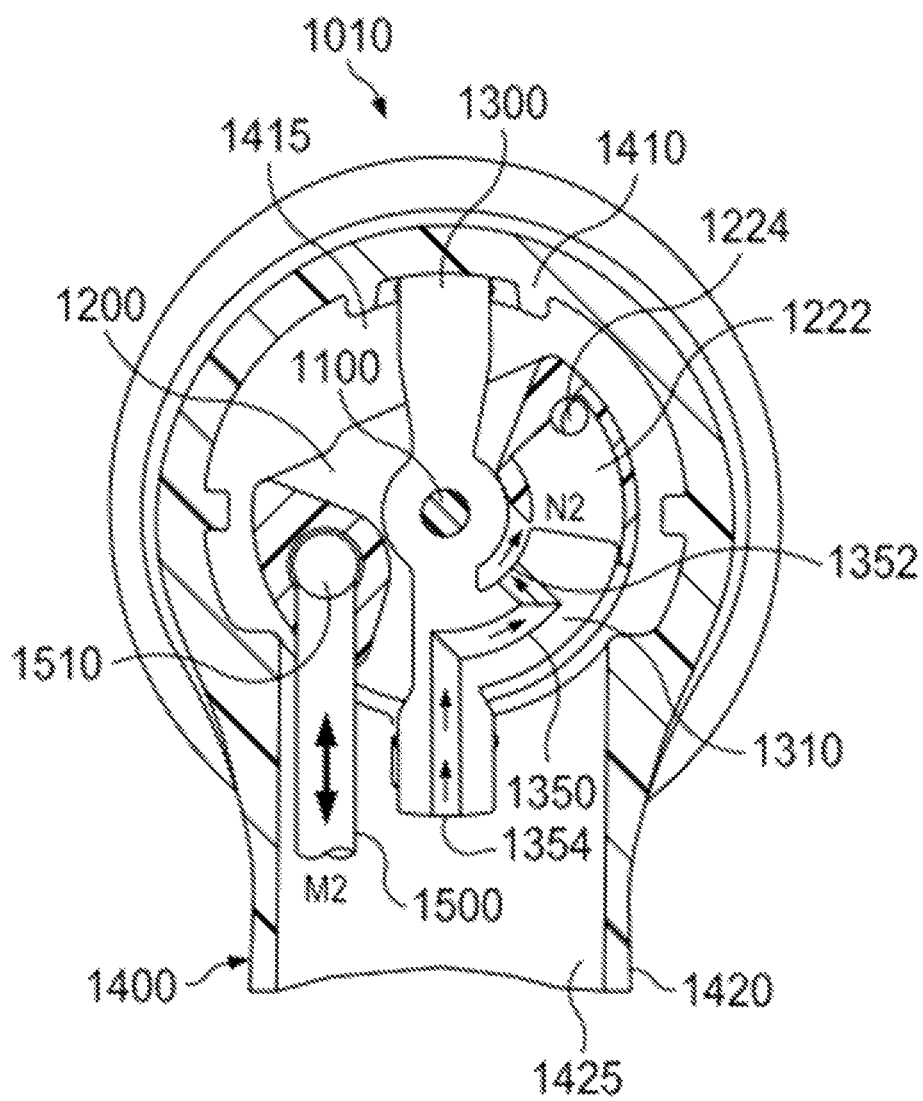
FIGS. 8A to 8C are sectional top views of the personal hygiene implement of FIG. 7, with the pump in its expansion, compression, and compressed positions, respectively, wherein a conduit is provided in the fixation element of the personal hygiene implement and the conduit is in fluid communication with the reservoir as shown in FIG. 7.
Figure 8B:
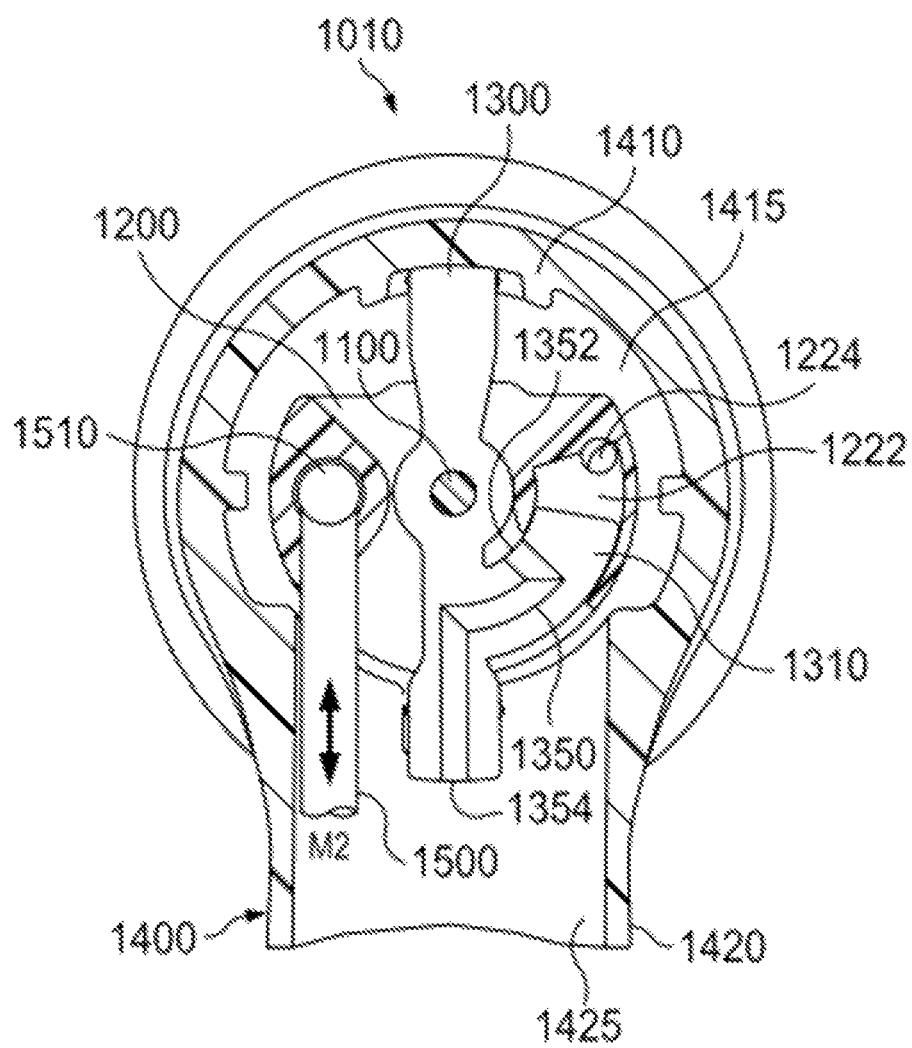
Figure 8C:
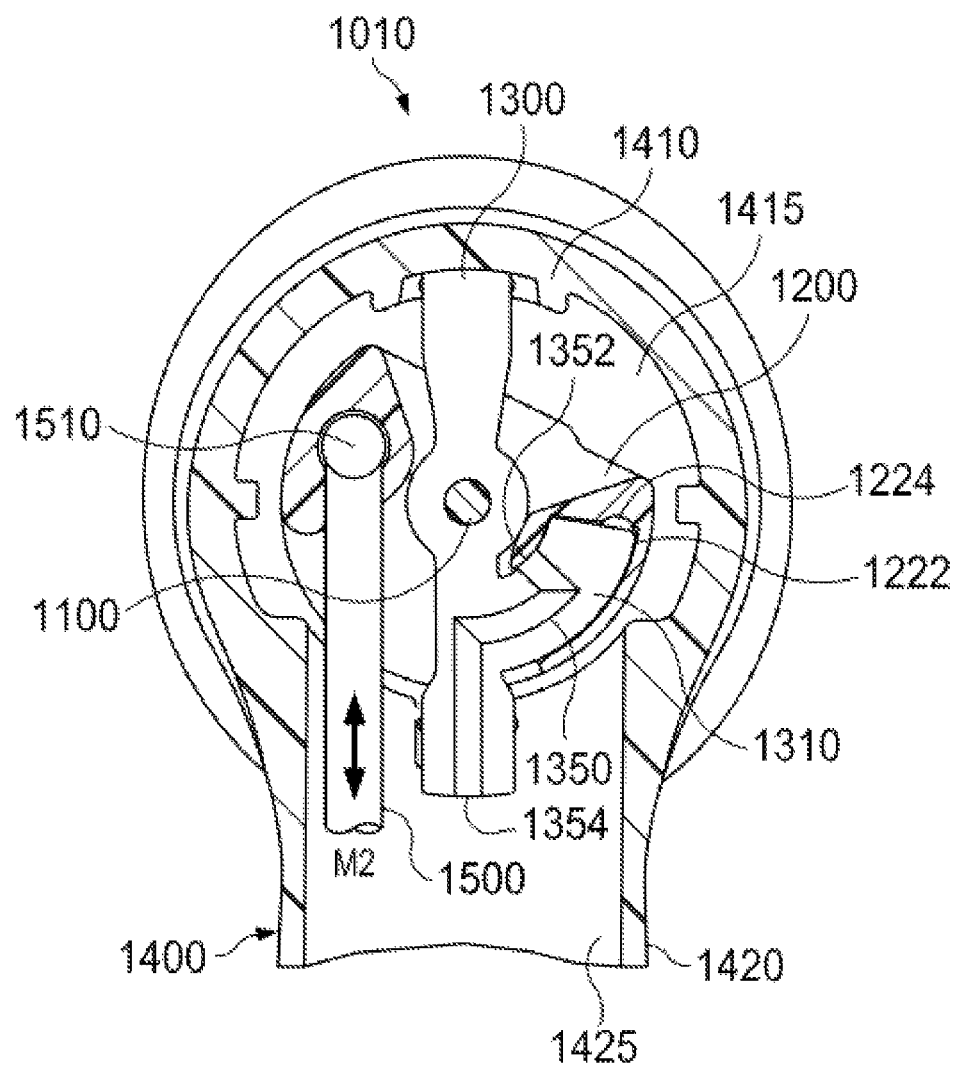

FIGS. 8A, 8B, and 8C are three sectional top views of the personal hygiene implement 1010 of FIG. 7, in which the fluid is fed from the reservoir 1600 (as shown in FIG. 7) to a pump of the present invention. The personal hygiene implement 1010 comprises an axle 1100, a movable functional element 1200, a fixation element 1300, a housing 1400, and a shaft element 1500. The housing 1400 has a head section 1410 and a neck section 1420 connected to the head section 1410. The head section 1410 has a head cavity 1415, and the neck section 1420 has a neck cavity 1425. The movable functional element 1200 comprises a piston chamber 1222. The fixation element 1300 comprises a piston 1310. The piston 1310 engages with the piston chamber 1222 to form the pump. The fixation element 1300 further comprises a conduit 1350. The conduit 1350 has an output end 1352 in fluid communication with the piston chamber 1222, and an input end 1354 in fluid communication with the reservoir 1600 (as shown in FIG. 7). FIGS. 8A, 8B, and 8C show three different steps during a single rotary oscillation cycle. When the shaft element 1500 (which may comprise a pivot pin 1510) goes to its lowest position (of a rotary oscillation cycle) as shown in FIG. 8A, the piston 1310 is outside of the piston chamber 1222 thereby exposing the output end 1352 of the conduit 1350. The fluid is drawn through the conduit 1350 into the piston chamber 1222 as indicated by the arrows N2 under the action of the negative pressure created in the piston chamber 1222. When the shaft element 1500 goes to a central position as shown in FIG. 8B (during a rotary oscillation cycle), the piston 1310 is inserted inside the piston chamber 1222 and a positive pressure is created in the piston chamber 1222. The positive pressure pushes the fluid inside the piston chamber 1222 out through a discharging through-hole 1224 and is ultimately directed to the first target surface by one or more outlets (not shown). Finally, when the shaft element 1500 goes to its highest position as shown in FIG. 8C, the piston 1310 compresses almost all the fluid out of the piston chamber 1222 and then the next rotary oscillation cycle is initiated as the shaft element 1500 returns back to its lowest position as shown in FIG. 8A.

It is to be noted that the various features that have been described in combination with other features for the different embodiments are meant to be disclosed as individual feature that shall be considered as being disclosed in all possible combinations with all other features as long as this does not contradict the gist and scope of the present disclosure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal hygiene implement (10, 1010) comprising:
   (a) an axle (100, 1100) that extends along a first longitudinal axis (L1);
   (b) a movable functional element (200, 1200) comprising:
      (i) a base (210) comprising a first side (212) and an opposing second side (214);
      (ii) a first pillar (220) extending from the first side (212) of the base (210), wherein the first pillar (220) comprises a piston chamber (222, 1222) that is fluidly connected to a discharging through-hole (224); and
      (iii) at least one cleaning element (240) extending from the second side (214) of the base (210); and
   (c) a fixation element (300, 1300) comprising a piston (310, 1310) which extends orthogonally to the first longitudinal axis (L1);
   wherein the movable functional element (200, 1200) is capable of rotatably oscillating around the axle (100, 1100), and the piston chamber (222, 1222) engages with the piston (310, 1310) to form a pump.

2. The personal hygiene implement (10, 1010) of claim 1, wherein the cleaning element is selected from the group consisting of a bristle tuft, an elastomeric element, a movably mounted plastic element, a tongue cleaning structure, and combinations thereof.

3. The personal hygiene implement (10, 1010) of claim 1, wherein the movable functional element (200, 1200) further comprises a second pillar (250) which protrudes from the first side (212) of the base (210) and which is connected with the first pillar (220) by a bridge (260) to define an opening (270) within the movable functional element (200, 1200).

4. The personal hygiene implement (10, 1010) of claim 3, wherein the fixation element (300, 1300) extends at least partially through the opening (270).

5. The personal hygiene implement (10, 1010) of claim 4, wherein the axle (100, 1100) has a first end (110) and an opposing second end (120), and the axle (100, 1100) extends through the movable functional element (200, 1200), and wherein the first end (110) of the axle (100, 1100) is affixed to the first side (212) and the second end (120) of the axle (100, 1100) is affixed to the bridge (260).

6. The personal hygiene implement (10, 1010) of claim 1, further comprising a housing (400, 1400) which comprises a head section (410) having a head cavity (415), and the fixation element (300, 1300) is affixed inside the head cavity (415).

7. The personal hygiene implement (10, 1010) of claim 6, wherein the housing (400, 1400) further comprises a neck section (420) connected to the head section (410), and the neck section (420) comprises a neck cavity (425, 1425), and wherein the fixation element (1300) comprises a conduit (1350) which has an output end (1352) in fluid communication with the piston chamber (1222), and an input end (1354) in fluid communication with a reservoir (1600) contained in the neck cavity (1425).

8. The personal hygiene implement (10, 1010) of claim 6, wherein the housing (400, 1400) further comprises a neck section (420) connected to the head section (410), and the neck section (420) comprises a neck cavity (425, 1425), and wherein the personal hygiene implement (10, 1010) further comprises a shaft element (500, 1500) extending through the neck cavity (425, 1425) into the head cavity (415), and wherein the movable functional element (200, 1200) has a shaft cavity (252) to receive the shaft element (500, 1500).

9. The personal hygiene implement (10, 1010) of claim 8, wherein the shaft cavity (252) extends into at least a portion of the bridge (260) or second pillar (250).

10. The personal hygiene implement (10, 1010) of claim 8, wherein the shaft element (500, 1500) engages with a drive unit to rotatably oscillate the movable functional element (200, 1200) around the axle (100, 1100) during operation.

11. The personal hygiene implement (10, 1010) of claim 1, further comprising a filter (234) disposed in fluid communication with the piston chamber (222, 1222).

12. The personal hygiene implement (10, 1010) of claim 11, wherein an inlet (232) is provided at the second side (214) and is in fluid communication with the piston chamber (222, 1222), and the filter (234) is disposed upstream of the inlet (232).

13. The personal hygiene implement (10, 1010) of claim 1, further comprising a metal material disposed in fluid communication with the piston chamber (222, 1222), wherein the metal material is selected from the group consisting of silver, copper, gold, rhodium, platinum, palladium, and combinations thereof.

14. The personal hygiene implement (10, 1010) of claim 1, wherein the piston chamber (222, 1222) has a volume from 1 mm$^3$ to 30 mm$^3$.

15. The personal hygiene implement (10, 1010) of claim 1, wherein an outlet (230) is provided at the second side (214) of the base (210) and has a cross-sectional area from 0.1 mm$^2$ to 4 mm$^2$, and wherein the piston chamber (222) is fluidly connected to the outlet (230) via the discharging through-hole (224).

16. The personal hygiene implement (10, 1010) of claim 1, wherein at least one cleaning element (240) comprises a hollow tube (242) and the outlet (230) opens into the hollow tube (242).

17. The personal hygiene implement (10, 1010) of claim 1, wherein the movable functional element (200, 1200) has a rotational degree of freedom around the axle (100, 1100) from 10 degrees to 60 degrees.

18. A personal hygiene implement, comprising:
(a) an axle that extends along a first longitudinal axis;
(b) a movable functional element comprising:
(i) a base comprising a first side and an opposing second side;
(ii) a first pillar extending from the first side of the base, wherein the first pillar comprises a piston which extends orthogonally to the first longitudinal axis; and
(iii) at least one cleaning element extending from the second side of the base; and
(c) a fixation element comprising a piston chamber that is fluidly connected to a discharging through-hole;
wherein the movable functional element is capable of rotatably oscillating around the axle, and the piston engages with the piston chamber to form a pump.

19. A personal hygiene device (1) comprising a handle (20) and a personal hygiene implement (10, 1010) according to claim 1 or 18 that is detachably or non-detachably attached to the handle (20), wherein the handle (20) comprises a drive unit arranged to drive the movable functional element (200, 1200) to rotatably oscillate around the axle (100, 1100) during operation.

* * * * *